US012782354B2

(12) United States Patent
Tlsty et al.

(10) Patent No.: US 12,782,354 B2
(45) Date of Patent: Nov. 3, 2026

(54) CANCER PROGRESSION RISK ASSESSMENT BY MICROVASCULAR PHENOTYPE

(71) Applicant: The Regents of the University of California, Oakland, CA (US)

(72) Inventors: Thea Tlsty, San Francisco, CA (US); Joseph Caruso, San Francisco, CA (US); Karla Kerlikowske, San Anselmo, CA (US); Annette Molinaro, San Francisco, CA (US); RosaAnna DeFilippis, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1232 days.

(21) Appl. No.: 17/423,583

(22) PCT Filed: Jan. 16, 2020

(86) PCT No.: PCT/US2020/013938

§ 371 (c)(1),
(2) Date: Jul. 16, 2021

(87) PCT Pub. No.: WO2020/150514

PCT Pub. Date: Jul. 23, 2020

(65) Prior Publication Data

US 2022/0107321 A1 Apr. 7, 2022

Related U.S. Application Data

(60) Provisional application No. 62/793,227, filed on Jan. 16, 2019.

(51) Int. Cl.
*G01N 33/57515* (2026.01)
*G01N 33/92* (2006.01)

(52) U.S. Cl.
CPC ....... *G01N 33/57515* (2026.01); *G01N 33/92* (2013.01); *G01N 2333/70596* (2013.01)

(58) Field of Classification Search
CPC ............. G01N 33/57415; G01N 33/92; G01N 2333/70596; G01N 2800/52
See application file for complete search history.

(56) References Cited

U.S. PATENT DOCUMENTS

| | | | |
|---|---|---|---|
| 6,852,537 B2 | 2/2005 | Hebbel | |
| 2003/0129663 A1 | 7/2003 | McGreggor | |
| 2005/0053590 A1 | 3/2005 | Meininger | |
| 2005/0112141 A1 | 5/2005 | Terman | |
| 2007/0099209 A1* | 5/2007 | Clarke | G01N 33/57484 435/6.12 |
| 2009/0209630 A1 | 8/2009 | Coleman et al. | |

FOREIGN PATENT DOCUMENTS

| | | | |
|---|---|---|---|
| WO | WO-2002/042426 A2 | 5/2002 | |
| WO | 2014015229 A1 | 1/2014 | |

OTHER PUBLICATIONS

Mwaikambo et al. Activation of CD36 Inhibits and Induces Regression of Inflammatory Corneal Neovascularization. Investigative Ophthalmology & Visual Science. 47(10): 4356-4364, Oct. 2006.*
DeFilippis et al. Cancer Discovery, Supplementary Figures, pp. 1-8, Sep. 2012.*
DeFilippis et al. Cancer Discovery, Supplementary Figure and Table Legends, pp. 1-27, Sep. 2012.*
Merriam-Webster's Dictionary of Law, 1 page (1996).*
Puchkova et al., Breast density as a risk factor of development of ductal carcinoma in situ. Clin. Experiment Surg. Petrovsky J. 7(2): 53-59, 2019.*
DeFelippis et al., 2012 CD36 Repression activates a multicellular stromal program shared by high mammographic density and tumor tissues, Cancer Discovry 2: 826-839.
Bremer et. al. A biologic signature for breast ductal carcinoma in situ to predict radiation therapy (RT) benefit and assess recurrence risk. Clin Cancer Res 10.1158/1078-0432.CCR-18-0842 (Jul. 27, 2018).
Rakovitch et. al. A population-based validation study of the DCIS Score predicting recurrence risk in individuals treated by breast-conserving surgery alone. Breast Cancer Res Treat (2015) 152:389-398 (Jun. 29, 2015).
Finak et. al Stromal gene expression predicts clinical outcome in breast cancer. Nature Medicine 14, pp. 518-527 (2008)]. (Apr. 27, 2008).
Uzzan et. al. Microvessel Density as a Prognostic Factor in Women with Breast Cancer. Cancer Res (2004)[Cancer Research 64, 2941-2955, (May 1, 2004).
Guidi et. al. Microvessel Density and Distribution in Ductal Carcinoma In Situ of the Breast. J Natl Cancer Inst. JNCI: Journal of the National Cancer Institute, vol. 86, Issue 8, pp. 614-619 (Apr. 20, 1994). (only abstract is available).
Brem et al., "Tumor Angiogenesis: A Quantitative Method for Histologic Grading," J Natl Cancer Inst., 48(2):347-356 (1972).
International Preliminary Report on Patentability from International Application No. PCT/US2020/013938 dated Jun. 16, 2021.

(Continued)

*Primary Examiner* — Alana Harris Dent
(74) *Attorney, Agent, or Firm* — MARSHALL, GERSTEIN & BORUN LLP

(57) ABSTRACT

Repression of CD36 vasculature in stromal tissues surrounding a pre-cancerous lesion provides is indicative of increased risk of subsequent progression to invasive cancer. Methods of assessing progression risk by measuring the abundance of CD36 vasculature in stromal tissues surrounding a precancerous lesion are provided, useful for various cancer types, including for assessing the risk of DCIS progression to breast cancer. Immunohistochemical analysis methods and diagnostic thresholds are provided, as well as associated methods of treatment and diagnostic kits.

7 Claims, 9 Drawing Sheets

(56) References Cited

OTHER PUBLICATIONS

International Search Report and Written Opinion from International Application No. PCT/US2020/013938 dated Oct. 27, 2020.

Uzzan et al., "Microvessel Density as Prognostic Factor in Women with Breast Cancer: A Systematic Review of the Literature and Meta-Analysis", Cancer Research, 64:2941-2955 (2004).

Weidner et al., "Tumor Angiogenesis and Metastasis—Correlation in Invasive Breast Carcinoma," N Engl J Med, 324, 8 pages (1991).

* cited by examiner

CANCER PROGRESSION RISK ASSESSMENT BY MICROVASCULAR PHENOTYPE

CROSS-RELATED APPLICATIONS

This application is a 35 USC § 371 national stage application of International Patent Application Serial Number PCT/US2020/013938, entitled "Cancer Progression Risk Assessment by Microvascular Phenotype," filed Jan. 16, 2020, which claims the benefit of priority to U.S. Provisional Application Ser. No. 62/793,227, entitled "Cancer Prediction by Microvascular Phenotype," filed Jan. 16, 2019 the contents of which are hereby incorporated by reference.

STATEMENT REGARDING FEDERALLY SPONSORED RESEARCH OR DEVELOPMENT

This invention was made with government support under grant nos. P01 CA107584, P50 CA058207, R01 CA163687, R01 CA187800, and R01 CA197977 awarded by the National Institutes of Health. The government has certain rights in the invention.

BACKGROUND OF THE INVENTION

Clinically, the occurrence of precancerous lesions in a subject presents a treatment dilemma. Although at significantly higher risk than subjects not diagnosed with a precancerous lesion, only a relatively small proportion of subjects with precancerous lesions will actually develop a potentially fatal invasive cancer (even if the subject is untreated). In current clinical practice, for example in the case of breast cancer, surgical and therapeutic modalities are broadly applied to the majority of women diagnosed with a precancerous lesion. Although these treatments reduce the risk of developing an invasive cancer, only a relatively small subset of women actually benefit from them. The majority of treated women, who would never develop an invasive cancer, are therefore being overtreated. An ability to accurately identify subjects diagnosed with pre-malignant conditions who are the most likely to benefit from aggressive therapy would allow clinicians to individualize therapy and reduce over/under treatment of subjects diagnosed with precancerous lesions.

Prognostic risk models based on biomarker detection and clinical information have long been utilized in clinical decision making for the treatment of patients with invasive cancers, including breast cancer. However, most of the biomarkers developed for directing therapy in invasive breast cancer have limited utility in informing treatment decisions for women diagnosed with DCIS. Recently, several biomarker-based assays have been developed, clinically tested, and commercialized to predict which women diagnosed with DCIS will recur and/or progress to invasive cancer. In published retrospective studies, for example, Bremer et. al. A biologic signature for breast ductal carcinoma in situ to predict radiation therapy (RT) benefit and assess recurrence risk. Clin Cancer Res (2018), and Rakovitch et. al. A population-based validation study of the DCIS Score predicting recurrence risk in individuals treated by breast-conserving surgery alone. Breast Cancer Res Treat (2015), results suggest that while existing biomarker assays can be used to more effectively direct radiation therapy (following lumpectomy) to a smaller subset of women, the sensitivity of these assays remains limited.

The majority of prognostic/predictive biomarkers utilized in clinical practice for patients diagnosed with both malignant and pre-malignant lesions directly assess the tumor epithelial cells. However, strong evidence suggests that the stromal component of the surrounding or adjacent tissue can also yield biomarkers capable of stratifying outcome and possibly directing therapy [see Finak et. al Stromal gene expression predicts clinical outcome in breast cancer. Nature (2008)]. For example, the quantitative measurement of microvessel density has been used to estimate the angiogenic activity of invasive tumor, for example, as described in Brem et. al Tumor angiogenesis: a quantitative method for histologic grading. J Natl Cancer Inst (1972). Several grading systems, for example the "hotspot" methodology first described in: Weidner et. al Tumor angiogenesis and metastasis—correlation in invasive breast carcinoma. N Engl J Med (1991), have been established for various tumor types. These typically rely on the use of specific antibodies that detect endothelial cells, including Von Willebrand factor (factor VIII), CD34, CD31, CD105, and vascular endothelial growth factor (VEGF) and varying techniques for calculating microvessel density.

Previous reports have examined the prognostic value of microvessel density in breast cancer and other tumor types. In patients diagnosed with invasive breast cancer, high microvessel density generally correlates with negative patient outcomes (to varying extents depending particularly on the antibody used and quantitative methodology), for example, reviewed in Uzzan et. al. Microvessel Density as a Prognostic Factor in Women with Breast Cancer. Cancer Res (2004). Although microvessel density has previously been evaluated in DCIS (as described in Guidi et. al. Microvessel Density and Distribution in Ductal Carcinoma In Situ of the Breast. J Natl Cancer Inst. (1994), this measure was shown to correlate with prognosis.

CD36 (also referred to platelet glycoprotein 4, fatty acid translocase (FAT), scavenger receptor class B member 3 (SCARB3), and glycoproteins 88 (GP88), IIIb (GPIIIB), or IV (GPIV)) is a multifunctional cell surface glycoprotein that acts as receptor for a diversity of ligands (e.g. thrombospondin, oxidized low-density lipoprotein, etc.). CD36 has been previously proposed as a prognostic marker for various types of cancer. The expression of CD36, although expressed by some tumor cells and rare epithelial compartments (e.g. in the stomach), is generally restricted to several stromal cell types, including adipocytes, macrophages, and endothelial cells where it plays a role in regulating angiogenesis, inflammation, and metabolism. Previous work implicates stromal downregulation of CD36 as a potential prognostic marker. For example, repression of stromal CD36 (including in microvessels) was previously observed in the breast tissue of women with high mammographic density (a known breast cancer risk factor) in the absence of cancer, as well as, in breast tumor tissues [as described in DeFilippis et. al. CD36 repression activates a multicellular stromal program shared by high mammographic density and tumor tissues. Cancer Discovery (2012)]). To date, however, CD36 has not been evaluated as risk stratification marker in DCIS in the context of microvessel density.

The state of the art in predicting DCIS progression to invasive breast cancer is illustrative of the treatment dilemma found across a range of neoplastic conditions. Overall, across various cancer types, the risk of overtreatment and undertreatment could be reduced if the risk of progression can be accurately predicted for subjects having precancerous lesions. Accordingly, there remains a need in the art for novel prognostic biomarkers methods to assess the likelihood of a subsequent invasive event in subjects having precancerous lesions, so that subjects may be directed to the most appropriate treatment, avoiding under-treatment and overtreatment harms and related expenses.

SUMMARY OF THE INVENTION

The prognostic methods disclosed herein provide the art with novel tools for assessing the likelihood of an invasive event in a subject having a precancerous lesion or cells. The methods and products disclosed herein are based upon the discovery that the abundance of CD36-expressing vasculature adjacent to a precancerous lesion is indicative of the risk of subsequent progression. Specifically, repression of CD36 in surrounding vasculature is indicative of increased risk of progression while abundant CD36-expressing vasculature in proximity to the lesion is indicative of reduced risk of progression.

In a first aspect, methods of assessing progression risk are provided that utilize the abundance of CD36-expressing vasculature surrounding or adjacent to a precancerous lesion as a predictive biomarker for assessing progression risk. Novel measures of CD36-expressing vasculature abundance and risk stratification thresholds are provided.

In a second aspect, methods of treatment based on the assessed risk of progression by the methods of the invention are provided, wherein appropriate treatment may be administered for subjects of differing progression risk.

In a third aspect, kits for the assessment of progression risk are provided, the kits being combinations of materials that facilitate facile measurement of the abundance of CD36-expressing vasculature in a sample.

The various methods and products disclosed herein may be applied in the prognosis of any number of cancers. In a primary embodiment, the inventions disclosed herein are directed to assessing progression risk in subjects having precancerous breast tissue, for example, DCIS.

DESCRIPTION OF THE FIGURES

FIG. 2A depicts distributions of endothelial vascular cell types in DCIS samples identified by palpation and FIG. 2B depicts distributions of endothelial vascular cell types in DCIS samples identified by mammogram.

FIG. 7A depicts the total area scoring positive for CD36 expression in DF breast vs. IBC. FIG. 7B depicts the total area scoring positive for CD36 expression for DCIS controls vs. cases. FIG. 7C depicts Kaplan-Meier plot with 95% confidence interval comparing the total event-free survival (any subsequent IBC) for patients stratified into groups with “high” or “low” CD36-area by the median. FIG. 7D depicts Kaplan-Meier plot with 95% confidence interval comparing the total event-free survival (subsequent IBC) for patients stratified into groups with “high” or “low” CD36-area by the median, but considering only regional or distant metastasis IBC events.

FIG. 8A depicts the total area scoring positive for CD31 expression in DF breast vs. IBC. FIG. 8B depicts the total area scoring positive for CD31 expression for DCIS controls vs. cases. FIG. 8C depicts Kaplan-Meier plot with 95% confidence interval comparing the total event-free survival (any subsequent IBC) for patients stratified into groups with “high” or “low” CD31-area by the median. FIG. 8D depicts Kaplan-Meier plot with 95% confidence interval comparing the total event-free survival (subsequent IBC) for patients stratified into groups with “high” or “low” CD31-area by the median, but considering only regional or distant metastasis IBC events.

DETAILED DESCRIPTION OF THE INVENTION

Figure 1A:
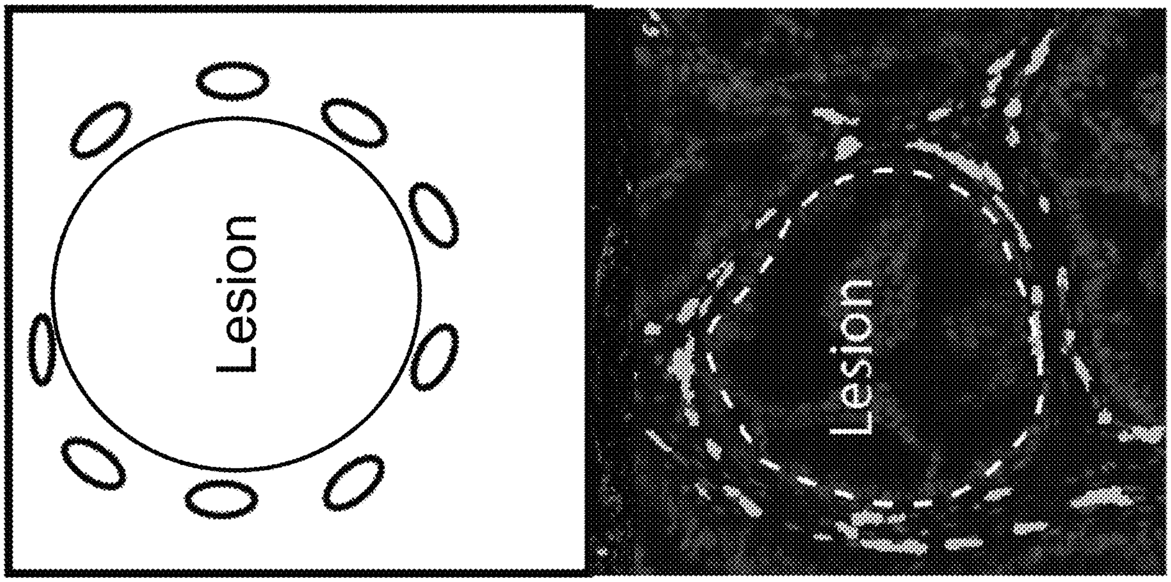
FIG. 1A depicts a diagrammatic representation (top) and grayscale version of microscope image (bottom) of a low risk lesion, wherein the lesion is substantially ringed by CD36-stained vascular elements in proximity to the border of the lesion.
Figure 1B:
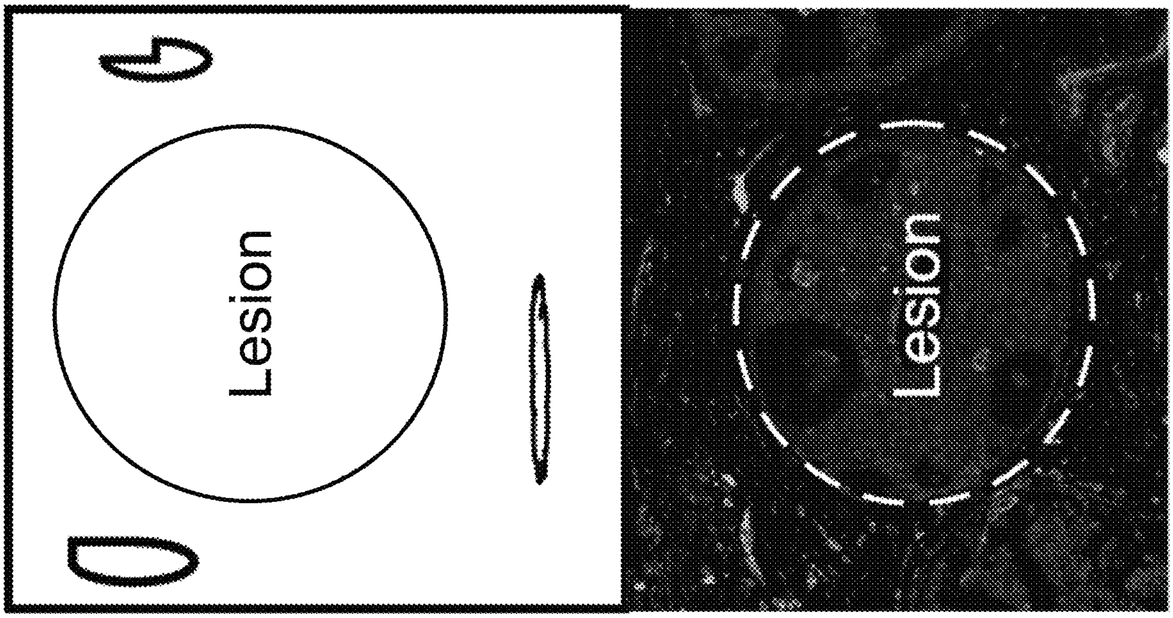
FIG. 1B depicts a diagrammatic representation (top) and grayscale version of microscope image (bottom) of a high risk lesion, wherein little or no CD36-stained vascular elements are in proximity to the border of the lesion and CD31-stained vasculature is found irregularly distributed around the lesion.
Figure 2A:
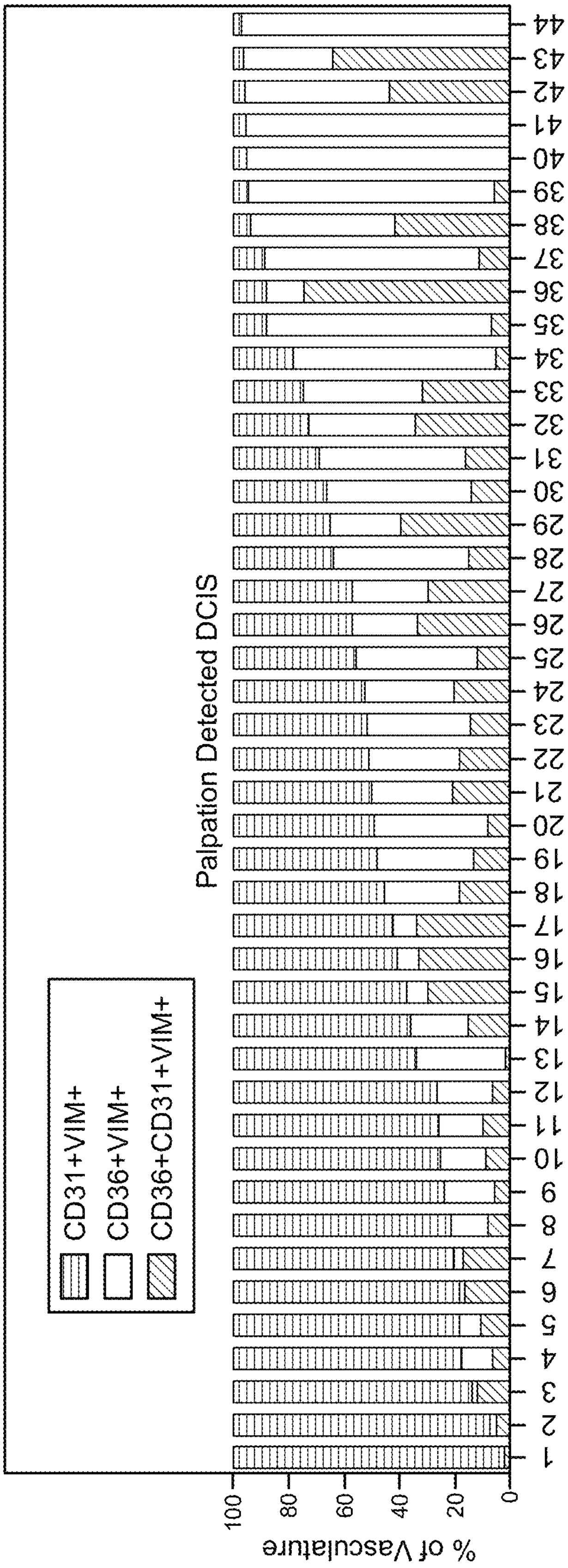
FIGS. 2A and 2B depict distributions of endothelial vascular cell types in a cohort of DCIS samples.
Figure 2B:
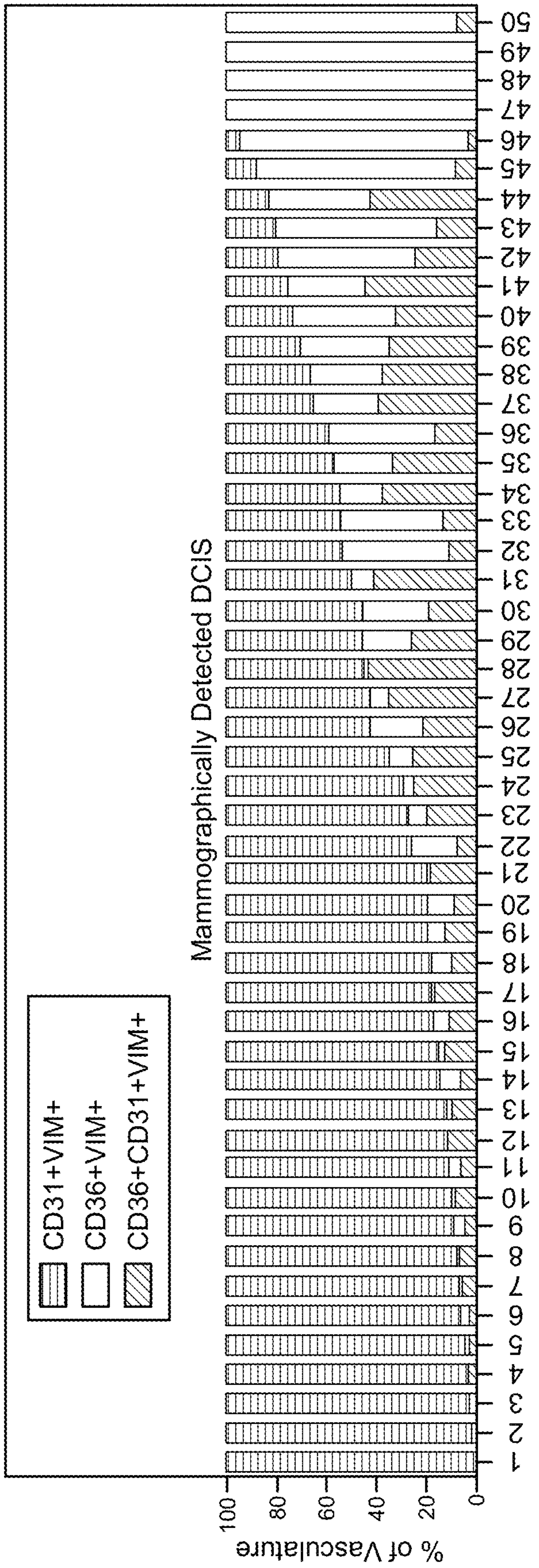
Figure 3:
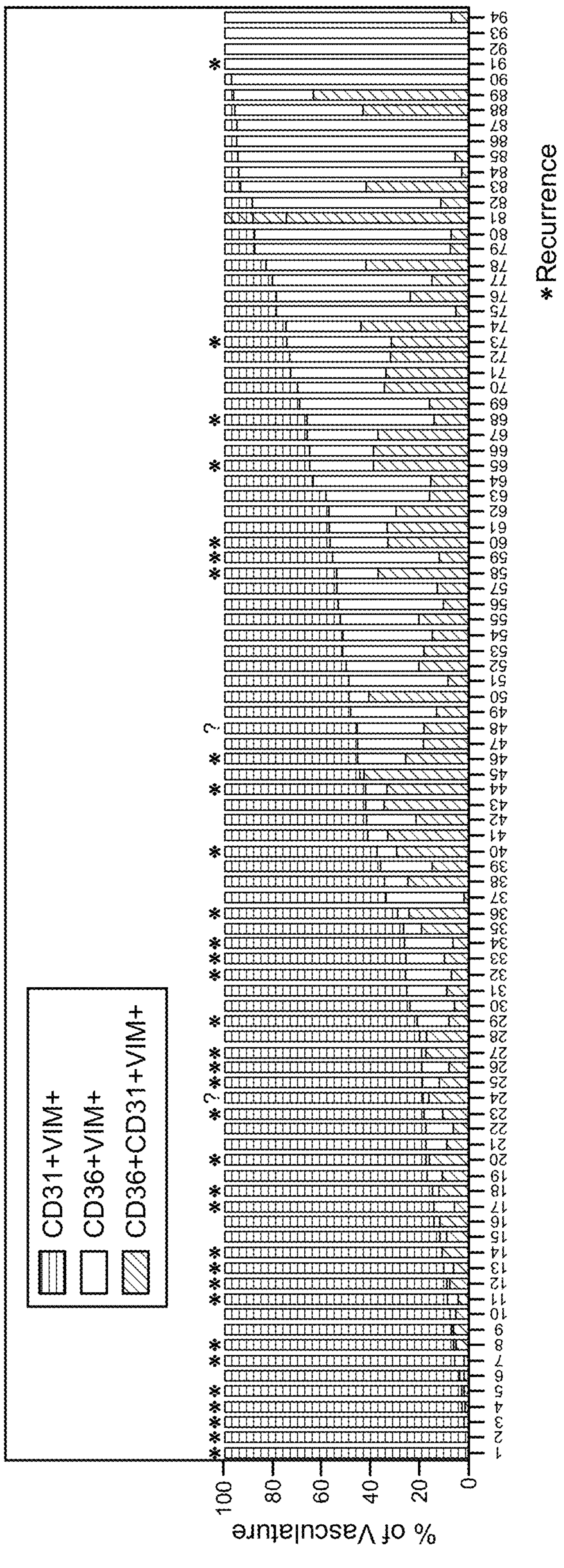
FIG. 3 depicts the distribution of $CD36^{+}/CD31^{-}$, $CD36^{+}/CD31^{+}$, and $CD36^{-}/CD31^{+}$ cell types in a cohort of DCIS samples. Asterisks denote samples from subjects that experienced subsequent recurrence as an invasive breast cancer.
Figure 4:
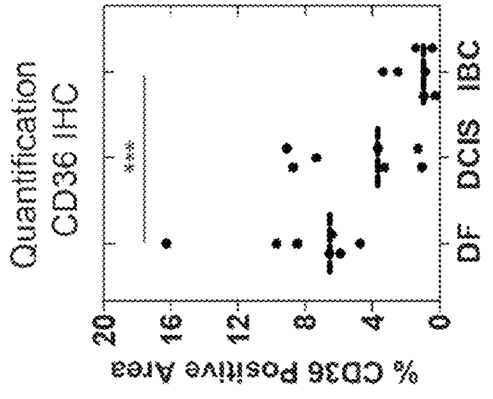
FIG. 4 depicts the loss of vascular endothelial CD36 expression during breast cancer progression. This graph depicts CD36-positive (DAB-stained) area expressed as a percentage of the total area for each specimen, from whole slide scans (20×) of DF breast, DCIS, and IBC probed (all n=7) with an antibody against CD36, developed with DAB and counterstained with hematoxylin.
Figure 5:
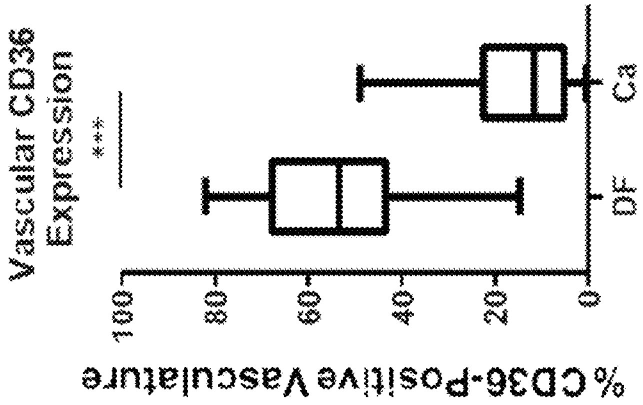
FIG. 5 depicts Repression of vascular endothelial CD36 that is characteristic of IBC. Representative images of DF breast tissue from five donors subjected to multiplex IHC for CD36, CD31, and vimentin and counterstained with DAPI. This graph depicts the total percentage of CD36 expressing phenotypes ($CD36^{+}vimentin^{+}$+$CD31^{+}CD36^{+}vimentin^{+}$) plotted for each DF breast and IBC.
Figure 6:
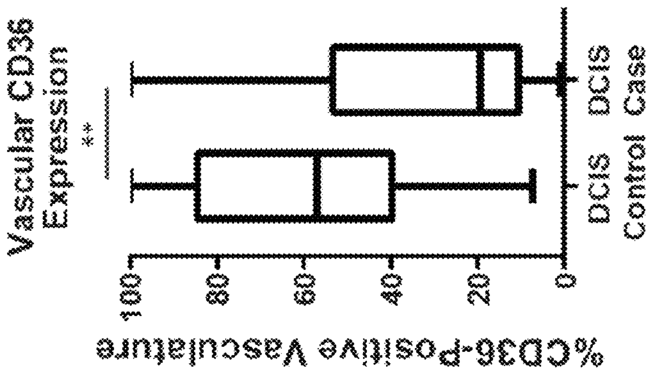
FIG. 6 depicts variable Vascular endothelial CD36 expression in DCIS. Representative images of DCIS from 10 donors were subjected to multiplex IHC for CD36, CD31, and vimentin, and counterstained with DAPI. This plot depicts the total percentage of CD36 expressing phenotypes ($CD36^{+}vimentin^{+}$+$CD31^{+}CD36^{+}vimentin^{+}$) plotted for DCIS controls and cases.
Figure 7A:
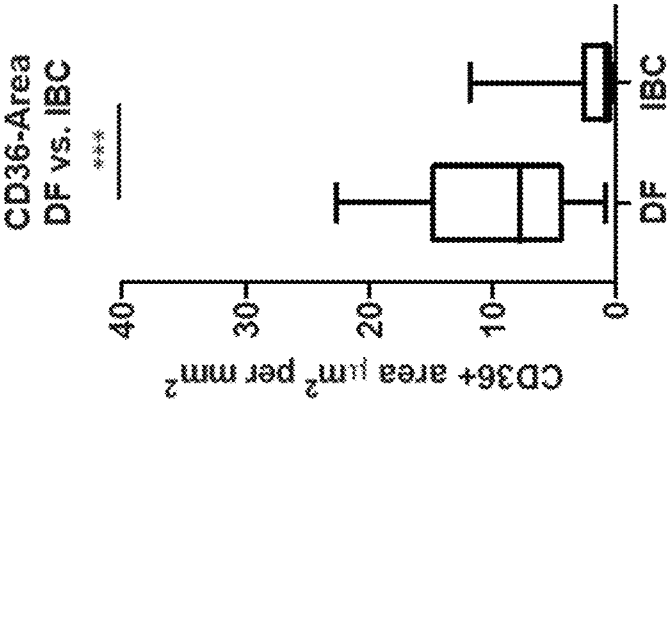
FIGS. 7A, 7B, 7C, and 7D demonstrate that vascular endothelial CD36 expression is predictive of the risk of a subsequent IBC in patients diagnosed with DCIS.
Figure 7B:
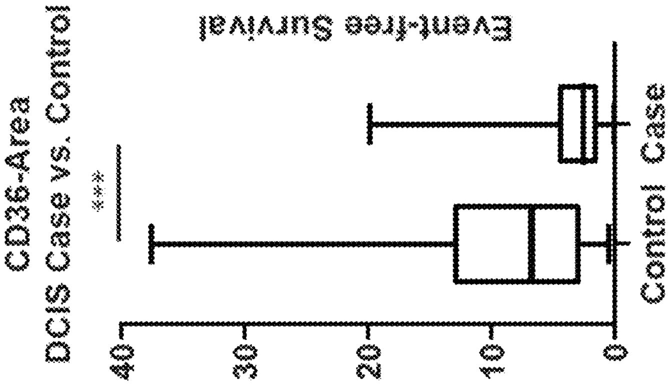
Figure 7D:
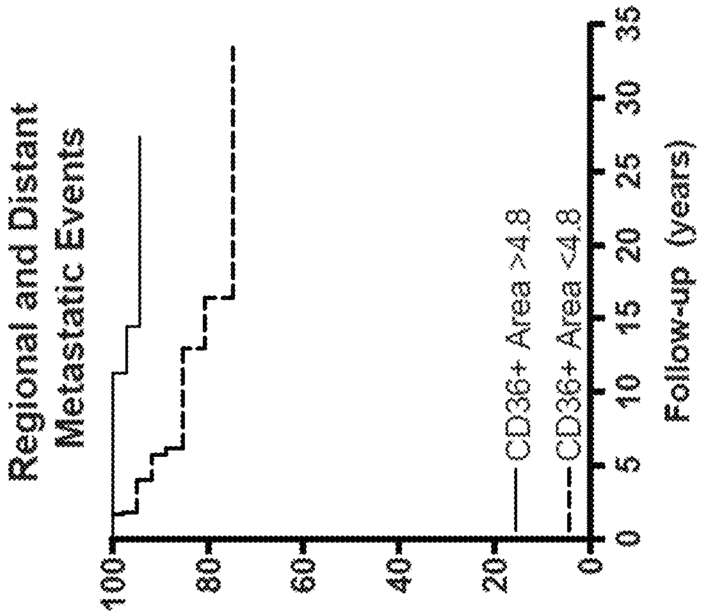
Figure 7C:
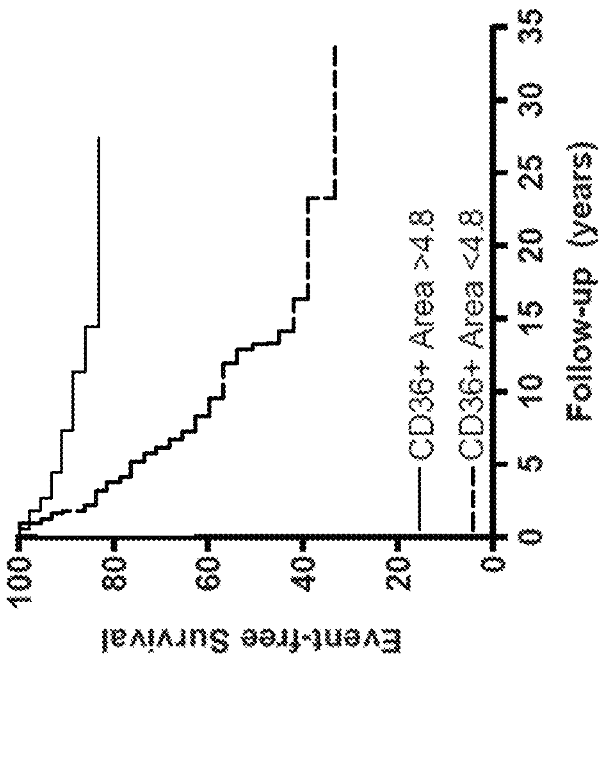
Figure 8B:
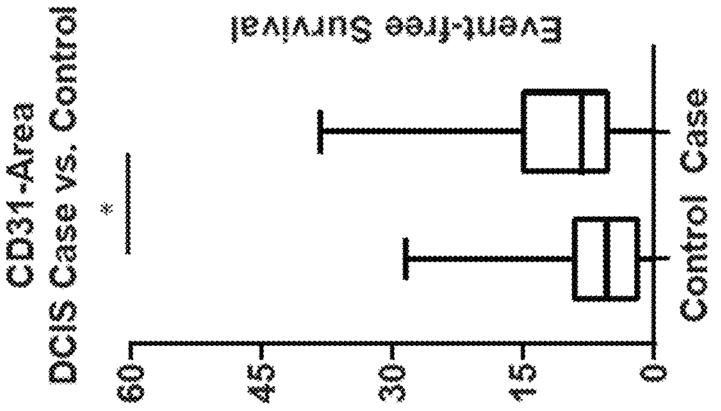
FIGS. 8A, 8B, 8C, and 8D demonstrate that vascular endothelial CD31 expression is not predictive of the risk of a subsequent IBC in patients diagnosed with DCIS.
Figure 8A:
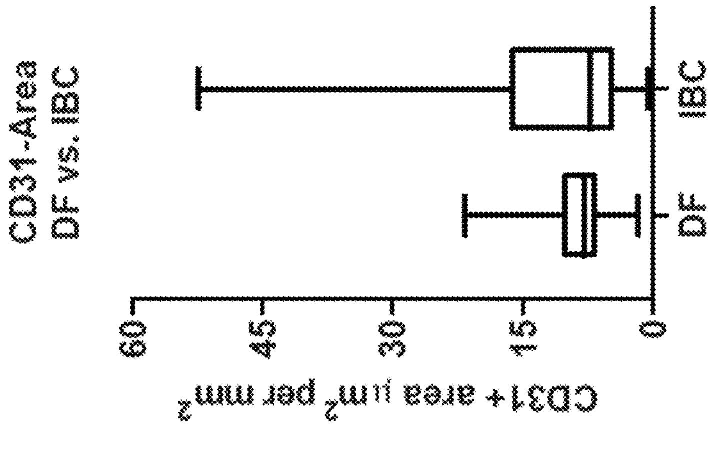
Figure 8D:
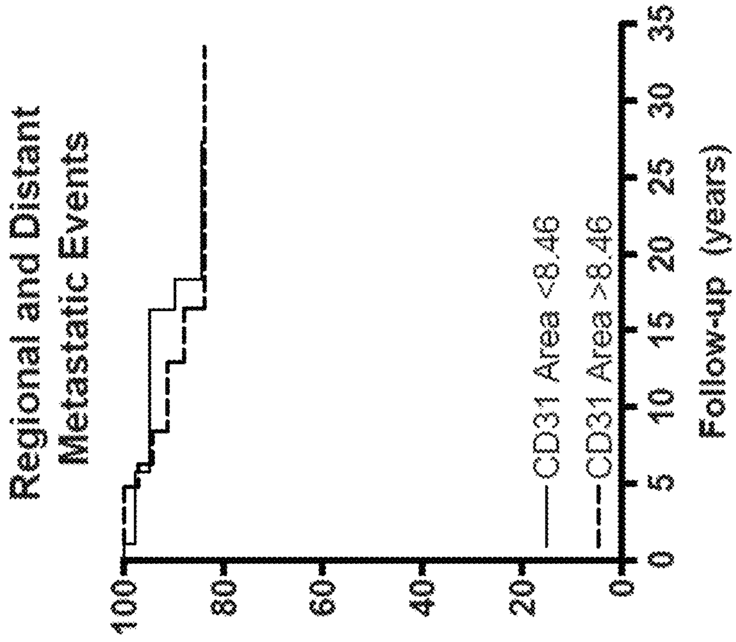
Figure 8C:
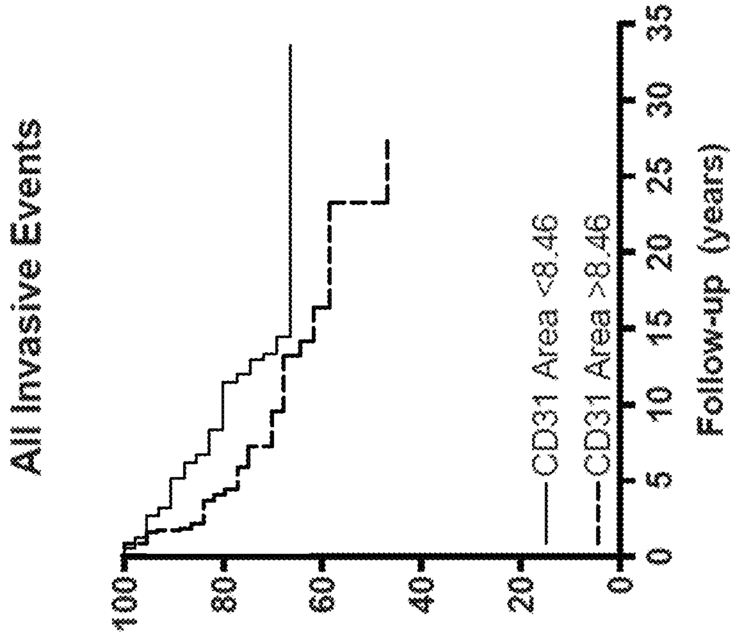

The methods and products of the invention disclosed herein are based on the observation that assessment of the abundance of CD36-expressing vasculature provides a measure for stratifying the risk of progression to invasive cancer in subjects having precancerous lesions. For example, in the context of breast tissues, the loss of CD36-expressing vasculature and a concomitant increase in the proportion of CD31-expressing vasculature adjacent to DCIS lesions predicts a high likelihood of a subsequent invasive event. Conversely, maintenance of CD36-expressing vasculature (and a comparatively lower level of CD31-expressing vasculature) in the DCIS lesion predicts a low likelihood of progression to invasive cancer.

As disclosed herein, the abundance of CD36-expressing vasculature in precancerous tissue provides a novel indicator of progression risk. This finding provides the art with a novel application of CD36 as a prognostic vasculature biomarker for DCIS and in other types of precancerous tissues besides breast. In contrast to previous assays looking at the prognostic significance of microvessel density alone, this assay is based on alterations in the hierarchical organization of the vascular network and the angiogenic proclivity of its components in order to extract prognostic information.

In a first aspect, the scope of the invention encompasses novel methods of assessing cancer progression risk by measuring the abundance of CD36-expressing vasculature, e.g. terminal vasculature such as capillaries, surrounding precancerous lesions. The general method of the invention encompasses the following steps for determining the risk of a subsequent invasive event in a subject with a pre-malignant lesion:

- a sample comprising a pre-malignant lesion and surrounding stromal tissue is obtained from the subject;
- the sample is analyzed to determine the abundance of CD36-expressing vasculature in the stromal compartment adjacent to the lesion;
- by the measured abundance of CD36-expressing vasculature, the risk of a subsequent invasive event in the subject is determined.

The various elements of the general method are described next.

Subjects and Cancer Types. The methods of the invention are applied for a subject. The subject may be a human, e.g. a human patient, or may be a non-human animal such as a test animal or veterinary subject.

The methods of the invention may be utilized for assessing the risk of progression from precancerous lesion to invasive cancer, for various cancer types. Cancer, as used herein, may encompass any neoplastic condition, including, for example, breast cancer, bladder cancer, brain cancer, cervical cancer, colorectal cancer, esophageal cancer, gastric cancer, head and neck cancer, kidney cancer, lung cancer, leukemia, lymphoma, myeloma, ovarian cancer, pancreatic cancer, prostate cancer, sarcoma, and skin cancer, including melanoma. The methods of the invention are well suited for the prognosis of cancers arising in epithelial cells.

The methods of the invention are directed to determining the "risk of cancer progression" Risk may be defined as the probability of a selected clinical outcome, over a selected timeframe, or as an increase in the probability of the selected clinical outcome probability over the probability of the clinical outcome in normal subjects. In a primary embodiment, the assessed risk is the probability of the lesion recurring as an invasive or malignant cancer, for example, arising de novo at or in proximity to the site of the original lesion or, or as a distal metastasis. In one embodiment, the assessed risk is the risk of a carcinoma in situ progressing to an invasive state. In one embodiment, the risk is the risk of recurrence as invasive cancer for a lesion that has been removed, for example, a DCIS lesion removed in a lumpectomy procedure. In one embodiment, in the case of an untreated lesion (not removed), the selected clinical outcome is the risk of the lesion progressing from a precancerous status to an invasive cancer status. In one embodiment, the risk is risk of mortality. In one embodiment, the risk is the probability of event-free survival.

Samples. The sample will be a tissue sample comprising stromal tissue adjacent to a precancerous lesion. As used herein, precancerous lesion will refer to any number of tissues or cells considered precancerous, premalignant, stage zero, or like descriptors. As used herein, a lesion may comprise an invasive cancer, including, for example, a tumor, or a pre-invasive lesion, including, for example, a carcinoma in situ.

In one embodiment, the cancer at issue is breast cancer, for example, invasive ductal carcinoma, and the sample stromal tissue adjacent to a DCIS lesion.

In one embodiment, the cancer is esophageal cancer, for example, adenocarcinoma, and the sample comprises stromal tissue adjacent to Barrett's esophagus tissue.

In one embodiment, the cancer is a gastrointestinal malignancy, for example, colorectal cancer, small bowel adenocarcinoma, intestinal lymphoma, anal cancer, or cholangiocarcinoma cancer, and the sample comprises stromal tissue adjacent to a colon polyp, metaplastic or dysplastic lesion, or tissue indicative of inflammatory bowel disease.

In one embodiment, the cancer at issue is skin cancer and the sample comprises an epidermal sample. In one embodiment, the cancer at issue is squamous cell carcinoma and the sample comprises stromal tissue adjacent to an actinic keratosis. In one embodiment, the cancer is intraepidermal squamous cell carcinoma and the sample comprises stromal tissue adjacent to squamous cell carcinoma tissue. In one embodiment, the cancer is melanoma and the sample comprises stromal tissue adjacent to a Lentigo maligna or a melanoma in situ.

In one embodiment, the cancer prostate cancer, and the sample comprises stromal tissue adjacent to a prostatic intraepithelial neoplasia or atypical small acinar proliferation and/or surrounding stromal tissue.

In one embodiment, the cancer at issue is ovarian cancer and the sample comprises stromal tissue adjacent to an ovarian cyst, fallopian tube STIC or p53-expressing lesion.

In one embodiment, the cancer is pancreatic cancer, and the sample comprises stromal tissue adjacent to a mucinous cystic neoplasm, intraductal papillary mucinous neoplasm, or solid pseudopapillary neoplasm.

In other embodiments, the cancer at issue is selected from lung, pancreas, cervix, brain, bladder, kidney, head and neck or hematopoietic malignancies and the precancerous tissue comprises a metaplastic or dysplastic lesion and/or surrounding stromal tissue typical of such cancers.

The sample may be obtained by means known in the art. For example, DCIS lesions may be collected by standard lumpectomy procedures. Other types of samples may be obtained by biopsy, excision, brushings, scrapings or resection techniques as relevant for the particular sample type and source tissue.

In a primary embodiment, the sample will contain both the lesion or a part thereof and surrounding stromal tissue. As used herein, "stromal tissue" surrounding a lesion or adjacent to a lesion comprises stromal cells, connective matrix, and vascular elements, including microvascular vessels. Tissue surrounding or in the vicinity of the lesion includes stromal tissue and vascular elements therein located within 1-10 mm from the border or edge of the lesion, for example, within about 1 mm, within about 2 mm, within about 3 mm, within about 4 mm, within about 5 mm, within about 6 mm, within about 7 mm, within about 8 mm, within about 9 mm, or within about 10 mm. "About," as used herein, encompasses an enumerated value, and in various embodiments, being substantially equivalent to the enumerated value, or being within plus or minus 5%, 10%, or 20% of the enumerated value.

In one embodiment, the sample is a freshly collected sample. In one embodiment, the sample is a banked sample. In one embodiment, the sample is a sample comprising epithelium and adjacent stroma (e.g., intralobular stroma in breast), for example, derived from a healthy disease-free subject, derived from an at-risk subject, or derived from a subject that previously underwent excision of precancerous tissue (e.g., a sample derived from at or near the resection area).

Analysis Techniques. The various methods and products of the invention encompass measurement of the abundance of a selected type of vasculature, for example, CD36-expressing vasculature or CD31-expressing vasculature, in the sample. "Vasculature," as used herein, in the context of the invention encompasses elements of the microcirculatory system, including microvessels such as arterioles, terminal arterioles, metarterioles, capillaries, and venules. In a primary implementation, the vasculature is terminal vasculature, for example, capillaries. These elements comprise endothelial cells that express one or more markers of vascular identity, such vimentin.

In the methods of the invention, vasculature is defined by and quantified by expression of one or more vascular markers. In a primary embodiment, vimentin is used as a marker of vascular identity. In alternative embodiments, vasculature is defined by and quantified by expression of any other vascular marker or markers, for example, in various embodiments, being Willebrand factor (factor VIII), CD34, and CD105.

In various implementations, described below, vasculature is classified by its expression of biomarkers probative of cancer progression risk. In the various embodiments of the invention, expression of CD36 is measured. CD36, also referred to platelet glycoprotein 4, fatty acid translocase (FAT), scavenger receptor class B member 3 (SCARB3), and glycoproteins 88 (GP88), IIIb (GPIIIB), or IV (GPIV), is a multifunctional cell surface glycoprotein that acts as receptor for a diversity of ligands (e.g. thrombospondin, oxidized low-density lipoprotein, etc.). CD36 expression is quantifiable by various means, including by the use of labeling agents selective for CD36, e.g. anti-CD36 antibodies comprising fluorescent or other labels, or epitopes for binding of labeled secondary antibodies. Exemplary anti-CD36 antibodies include anti-CD36 antibody D8L9T, Rabbit mAb #14347 (Cell Signaling Technology, Danvers, MA USA).

In one embodiment, the abundance of CD36-expressing vasculature is assessed by measuring the abundance of a CD36 proxy, meaning a biomarker whose abundance is highly correlated with CD36 expression.

In the various embodiments of the invention, expression of CD31 is measured. CD31, also known as Platelet endothelial cell adhesion molecule (PECAM-1), is expressed in endothelial cells, for example, vascular endothelial cells. CD31 expression is quantifiable by various means, including by the use of labeling agents selective for CD31, e.g. anti-CD31 antibodies comprising fluorescent or other labels, or epitopes for binding of labeled secondary antibodies.

In one embodiment, the abundance of CD31-expressing vasculature is assessed by measuring the abundance of a CD31 proxy, meaning a biomarker whose abundance is highly correlated with CD31 expression.

Various platforms for classifying and quantifying vasculature may be used. In a primary implementations, the identification will be by immunolabeling. In immunohistochemical analysis, one or more selected markers are targeted by a selective labeling agent. The selective labeling agent is a composition of matter which selectively binds to, or otherwise associates with a target antigen, such as a vascular marker, CD36, or CD31, and which comprises a means of visualizing, quantifying, or otherwise detecting the labeling agent. The selective labeling agent may comprise antibodies, antibody fragments, or antibody mimics, wherein the composition comprises recognition elements (e.g. antigen-binding regions of antibodies or variants thereof) which selectively bind to the target antigen with high affinity. Exemplary labeling agents will comprise a detectable species such a fluorescent labels, such as a fluorescent protein, fluorescent dye, or fluorophore. Exemplary fluorescent labels include green fluorescent protein, red fluorescent protein, yellow fluorescent protein, fluorescein isothiocyanate, fluorescin, FITC, PE, PerCP, Rhodamine, aminomethylcoumarin, R-phycoerythrin, and fluorochrome dyes, as known in the art. Exemplary fluorescent dyes include ALEXA FLUOR™ (Invitrogen) dyes. In other implementations, the detection moiety may comprise an enzyme for detection and quantification assays, exemplary enzymes including, for example, horseradish peroxidase, alkaline phosphatase, urease, and other enzymatic detection systems known in the art. In some implementations, the detection moiety comprises an affinity tag, an epitope tag for binding of secondary labeled antibodies or other moieties such as agents used in immunofluorescent methods, immunostaining, flow cytometry, and like methods. Other detection moieties include oligonucleotides, such as DNA barcodes.

In a primary embodiment, the sample will comprise a tissue section which is analyzed by immunofluorescence. The use of tissue sections enables analysis of morphology in the sample as well as quantification of cell types in the sample. Tissue samples may be analyzed by immunofluorescence imaging as known in the art, for example, by fluorescence microscopy, for example, by confocal laser scanning microscopy. Such analyses enable observation of morphology, branching pattern, and proximity to the epithelium.

In alternative embodiments, the sample is analyzed by techniques which quantify the number of cells within a specific category, for example, by dissociation of the sample and subsequent cell sorting, such as by flow cytometry or single-cell transcriptome analysis.

In alternative embodiments, quantitative PCR is utilized to assess vascular marker expression, CD36 expression, and, optionally, CD31 expression. For example, cells in the tissue may be barcoded to preserve spatial information, and subsequently may be dissociated and analyzed by quantitative PCR to assess relative abundance of CD36 expressing vascular elements.

In the analysis, cells that are not relevant to the analysis, for example, adipocytes expressing both vimentin and CD36, are easily removed from the analysis based on morphology or the expression of adipocytic markers. These can be manually blocked or excluded from quantification of CD36 label in analyses of tissue sections based on morphology. In cell counting or gene expression assays, expression of adipocyte markers may be used to quantify and subtract adipocyte-based CD36 signal, for example, adipocytic markers such as leptin, HOXC8, HOXC9, Ucp1, CIDEA, PRDM16, Zic1, Lhx8, Eva1, Epsti1, Cd137, Tmem26, Tbx1, Cited1, and Shox2.

The analysis may be performed in a selected "analysis area" of the sample. Generally, the most probative cells will be stromal tissues adjacent to or in close proximity to the lesion, or, in the case of healthy tissues, the stromal tissues adjacent to epithelial cells borders. Cells in proximity to a lesion (or epithelial border) may encompass tissue or cells within 1-10 mm of the lesion border (or epithelial border). For example, in various embodiments, the analysis area comprises stromal cells within a defined area or volume of tissue that is within 0.1 mm, 0.2 mm, 0.3 mm, 0.4 mm, 0.5 mm, 0.6 mm, 0.7 mm, 0.8 mm, 0.9 mm, 1.0 mm, 1.2 mm, 1.5 mm, or 2.0 mm of the selected boundary.

Multiple analysis areas may be analyzed in a single sample, for example, 2, 3, 4, 5, 6, 7, 8, 9, or 10 regions, for example, selected in a tissue section, and statistical analyses known in the art may be applied to determine average, mean, median, or other measures of abundance of selected tissue types.

Measures of CD36 Vasculature Abundance. In the methods of the invention, progression risk, as described herein, is assessed by determining the abundance of CD36-expressing vasculature in the stromal compartment surrounding or adjacent to the lesion.

In a first implementation, the abundance of CD36-expressing vasculature is a measurement of the relative abundance of CD36-expressing vasculature: comprising a measurement of the proportion of vasculature in the analysis area of the sample which is CD36-expressing vasculature. In a primary embodiment, the relative abundance of vasculature expressing CD36 is measured as proportion of vasculature expressing CD36 against total vasculature in the analysis area, including both CD36-expressing and CD31-expressing vasculature. As disclosed herein, at-risk lesions tend to have a higher proportion of CD31-expressing vasculature and relatively less CD36-expressing vasculature, while low-risk lesions tend to have a higher proportion of CD36-expressing vasculature and relatively less CD31-expressing vasculature.

For both high risk and low risk lesions, typically, a minority proportion of the vasculature is both CD36-expressing and CD31-expressing vasculature. This vasculature will be termed herein as CD36+/CD31+ vasculature. For example, in some tissues, CD36+/CD31+ vasculature averages about 5-20% of total vasculature, in one embodiment, total vasculature being the sum of all vasculature expressing CD36, CD31, or both CD36 and CD31.

In one embodiment, the relative abundance of CD36-expressing vasculature cells in the analysis area of the sample is determined as the following ratio (or its mathematical equivalent):

$$\frac{[CD36+/CD31-]+[CD36+/CD31+]}{[CD36+/CD31-]+[CD36+/CD31+]+[CD36-/CD31+]}$$

wherein [CD36$^+$/CD31$^-$] denotes the abundance of CD36-positive-CD31-negative vasculature in the analysis area of the sample, [CD36$^+$/CD31$^+$] denotes the abundance of CD36-positive-CD31-positive vasculature in the analysis area of the sample, and [CD36–/CD31$^+$] denotes the abundance of CD36-negative-CD31-positive vasculature in the analysis area of the sample.

In an alternative embodiment, the relative abundance of CD36-expressing vasculature cells in the analysis area of the sample is determined as the following ratio (or its mathematical equivalent):

$$\frac{[CD36+/CD31-]}{[CD36+/CD31-]+[CD36+/CD31+]+[CD36-/CD31+]}$$

wherein [CD36$^+$/CD31$^-$] denotes the abundance of CD36-positive-CD31-negative vasculature in the analysis area of the sample, [CD36$^+$/CD31$^{+]}$ denotes the abundance of CD36-positive-CD31-positive vasculature in the analysis area of the sample, and [CD36–/CD31$^+$] denotes the abundance of CD36-negative-CD31-positive vasculature in the analysis area of the sample.

In another embodiment, the relative abundance of CD36-expressing vasculature cells in the sample is determined as the following ratio (or its mathematical equivalent):

$$\frac{[CD36+/CD31-]}{[CD36+/CD31-]+[CD36-/CD31+]}$$

wherein [CD36$^+$/CD31$^-$] denotes the abundance of CD36-positive-CD31-negative vasculature in the analysis area of the sample, [CD36–/CD31$^+$] denotes the abundance of CD36-negative-CD31-positive vasculature in the analysis area of the sample, and the abundance of CD36-positive-CD31-positive vasculature in the analysis area of the sample is omitted.

In another embodiment, the relative abundance of CD36-expressing vasculature cells in the sample is determined as the following ratio (or its mathematical equivalent):

$$\frac{[CD36+]}{[\text{total vasculature}]}$$

wherein [CD36$^+$] denotes the abundance of CD36-positive vasculature, and [total vasculature] denotes the abundance of all vasculature in the sample, i.e., expressing a vascular marker. In one embodiment, [CD36$^+$] is replaced with [CD36$^+$/CD31$^-$] in the calculation.

In addition to the proportional measures disclosed above, the scope of the invention encompasses an alternative measure of abundance of CD36-expressing vasculature, comprising a measurement of the total CD36-expressing vasculature signal in the analysis area. For example, in one implementation, total CD36-expressing vasculature is measured in a tissue section and quantified by area. This measurement can be normalized to the measured area of the analysis area. For example, in one embodiment, the abundance of CD36-expressing vasculature is measured as the total staining area of CD36 normalized to the total analysis area, for example, expressed as $\mu m^2$ per $mm^2$.

In an alternative implementation, the arrangement of CD36-expressing vasculature around the lesion is used as an indicator of progression risk. The inventors of the present disclosure have determined that the presence of CD36-staining vasculature surrounding a substantial portion of the lesion, i.e. in a ring, is indicative of reduced progression risk. Conversely, the lack of surrounding CD36-expressing vasculature is indicative of elevated progression risk. The presence or absence of a ring of CD36-expressing vasculature in contact with or in close proximity to the lesion can be scored qualitatively by eye, or quantitatively, for example, by the percentage of the lesion diameter that is surrounded by CD36-expressing tissue, with, in some embodiments greater than 30%, 40%, 50%, 60%, 70%, 80%, or 90%, surrounding CD36-expressing vasculature being indicative of reduced progression risk.

Risk Thresholds and Determination. After the abundance of CD36-expressing vasculature is measured by the selected method, the measured value is compared against one or more risk thresholds to provide an assessment of risk.

In general, if the measured abundance of CD36-expressing vasculature is low or suppressed, relative to its abundance in healthy, disease free tissue, this is indicative of an increased risk of progression. "Low," "reduced," "suppressed" or otherwise diminished abundance may be defined by any number of selected threshold values. In one embodiment, low abundance of CD36-expressing vasculature is defined as a measured value below the median or mean abundance value for like, disease-free tissues, for example, in various embodiments, being: at least 20% lower than the median or mean, at least 30% lower than the median or mean, at least 40% lower than the median or mean, at least 50% lower than the median or mean, at least 60% lower than the median or mean, at least 70% lower than the median or mean, at least 80% lower than the median or mean, at least one standard deviation below the median or mean, at least two standard deviations below the median or mean, at least three standard deviations below the median or mean, being below the 95% confidence interval of the mean, or any other statistically relevant measure of "reduced" relative to abundance in like, disease-free tissues.

Risks may be assessed a probability scores, for example, the likelihood of progression to a selected clinical outcome, for example, occurrence per year, or over a selected time interval, for example, the probability of event free survival over two years, five years, ten years, fifteen years, twenty years, or any other selected timeframe. Risk may alternatively be assessed as a categorical stratification, e.g., increased risk, low risk, high risk, for example, associated with probabilities or confidence intervals. Risk may be defined as an elevated risk, for example, an elevated risk of progression invasive cancer over the risk of developing invasive cancer in subjects that do not have precancerous lesions, or the risk seen in the general population or a population of matched subjects (e.g. matched by medical history, demographics, or other factors).

The risk assessment methods of the invention utilize observed relationships between the selected measure of CD36-expressing vascular abundance and the selected outcome, e.g., probability of an invasive event. This relationship may be readily established retrospectively by analysis of precancerous samples derived from subjects wherein the outcome of the subject is known. The relationship may be established for a selected cancer type, selected precancerous tissue sample type, and selected population of subjects (e.g. subjects having a common demographic or health profile). From retrospective analysis of these samples, a mathematical association between the proportion of CD36-expressing vasculature and a subsequent invasive event may be derived.

In one embodiment, thresholds for elevated risk of an invasive event may be established. For example, cutoff value may be calculated, wherein a measured abundance of CD36-expressing vasculature value falling below the selected threshold value is indicative of poor prognosis, elevated risk of an invasive event, or decreased event-free survival. Alternatively, a classifier model may be generated, which may be applied to measured CD36 abundance data to classify the subject's progression or other risk, for example, low or elevated risk. In another embodiment, a predictive model is generated wherein the input is the measured abundance of CD36-expressing vasculature and the output is the likelihood of the subject progressing to invasive cancer. Thresholds and classification schemes may be implemented with selected specificity and sensitivity parameters, as known in the art.

The thresholds, classifier models, or predictive models may be generated by any suitable statistical tools known in the art. For example, the relationship between the proportion of CD36-expressing vasculature and progression may be established using statistical methods such as: logistic regression analysis, linear discriminate analysis, partial least squares-discriminate analysis, multiple linear regression analysis, multivariate non-linear regression, backwards stepwise regression, threshold-based methods, tree-based methods, generalized additive models, supervised and unsupervised learning models, cluster analysis, and other statistical model generating methods known in the art.

In one implementation, the selected measure of CD36-expressing vasculature abundance is the proportion CD36-expressing vasculature to total CD31-expressing, CD36-expressing, and CD31+/CD36+ vasculature, for example:

$$\frac{[CD36+/CD31-]+[CD36+/CD31+]}{[CD36+/CD31-]+[CD36+/CD31+]+[CD36-/CD31+]}$$

or an equivalent measure. In such implementation, the selected risk may be the risk of progression, for example, the risk of progression from DCIS to invasive breast cancer in the case of breast lesions, and the selected cutoff value defining low and high risk may be a value between 5 and 75%, for example, between 10% and 60%, for example, a value between 10 and 20%, a value selected from 5%, 6%, 7%, 8%, 9%, 10%, 11%, 12%, 13%, 14%, 15%, 16%, 17% 18%, 19%, a value between 20 and 25%, a value between 25 and 30% a value between 30 and 35% or less, a value between 35% and 40%, a value between 40% and 45%, a value between 45% and 50%, a value between 50 and 55%, a value between 55 and 60%, a value between 60% and 65%, a value between 65% and 70%, or a value between 70% 75%, wherein a measured abundance of CD36-expressing vasculature below the selected threshold value is indicative of increased risk of progression and a measured abundance of CD36-expressing vasculature above the selected threshold value is indicative of decreased risk of progression, for example, increased risk in one embodiment being an increase in risk of experiencing progressive cancer over the population average or over the risk observed in subjects without precancerous lesions. In one embodiment, the selected threshold value is between 60 and 70%, for example 60%, 61%, 62%, 63%, 64%, 65%, 66% 67%, 68%, 69% or 70%. In one embodiment, the selected threshold value is 66%. Subjects with measured CD36-expressing vasculature abundance below the cutoff value may have an elevated risk of progression wherein elevated risk is defined as a 25%, 50%, 7%, 100% 150%, 200%, 300%, 400%, 500% greater risk of progression than subjects having CD36-expressing vasculature abundance above the cutoff value.

In one implementation, the selected measure of CD36-expressing vasculature abundance is total staining area of CD36 (or CD36+/CD31+, or CD36+/CD31+/vimentin+) normalized to the total assay area ($\mu m^2$ per $mm^2$). In such implementation, the selected risk may be the risk of progression to invasive breast cancer, and the selected cutoff value stratifying elevated risk may be a value between 2 and 80 $\mu m^2$ per $mm^2$, for example, at about 2.0 $\mu m^2$ per $mm^2$, about 2.5 $\mu m^2$ per $mm^2$, about 3.0 $\mu m^2$ per $mm^2$, about 3.5 $\mu m^2$ per $mm^2$, about 4 $\mu m^2$ per $mm^2$, about 4.5 $\mu m^2$ per $mm^2$, about 5 $\mu m^2$ per $mm^2$, about 5.5 $\mu m^2$ per $mm^2$, about 6.0 $\mu m^2$ per $mm^2$, about 6.5 $\mu m^2$ per $mm^2$, about 7.0 $\mu m^2$ per $mm^2$, about 7.5 $\mu m^2$ per $mm^2$, about 8.0 $\mu m^2$ per $mm^2$, about 9.0 $\mu m^2$ per $mm^2$, about 10 $\mu m^2$ per $mm^2$, about 11 $\mu m^2$ per $mm^2$, about 12 $\mu m^2$ per $mm^2$, about 13 $\mu m^2$ per $mm^2$, about 14 $\mu m^2$ per $mm^2$, about 15 $\mu m^2$ per $mm^2$, about 16 $\mu m^2$ per $mm^2$, about 17 $\mu m^2$ per $mm^2$, about 18 $\mu m^2$ per $mm^2$, about 19 $\mu m^2$ per $mm^2$, about 20 $\mu m^2$ per $mm^2$, about 21 $\mu m^2$ per mm$^2$, about 22 μm$^2$ per mm$^2$, about 23 μm$^2$ per mm$^2$, about 24 μm$^2$ per mm$^2$, about 25 μm$^2$ per mm$^2$, about 26 μm$^2$ per mm$^2$, about 27 μm$^2$ per mm$^2$, about 28 μm$^2$ per mm$^2$, about 29 μm$^2$ per mm$^2$, about 30 μm$^2$ per mm$^2$, between 30 and 35 μm$^2$ per mm$^2$, between 35 and 40 μm$^2$ per mm$^2$, between 45 and 50 μm$^2$, between 50 and 55 μm$^2$ per mm$^2$, between 55 and 60 μm$^2$ per mm$^2$, between 60 and 65 μm$^2$ between 65 and 70 μm$^2$, between 70 and 75 μm$^2$ per mm$^2$, and between 75 and 80 μm$^2$ per mm$^2$, wherein a measured abundance of CD36-expressing vasculature below the selected threshold value is indicative of increased risk of progression and a measured abundance of CD36-expressing vasculature above the selected threshold value is indicative of decreased risk of progression. Subjects with measured CD36-expressing vasculature abundance below the cutoff value may have an elevated risk of progression, for example, at least 25%, at least 50%, at least 100% at least 150%, at least 200%, at least 300%, at least 400%, or at least 500% greater risk of progression than subjects without precancerous lesions, the general population risk, or subjects having CD36-expressing vasculature abundance above the cutoff value.

In one embodiment, the subject is a subject with DCIS and the selected cutoff value defining low and high risk may be a value between 2 and 8 μm$^2$ per mm$^2$, for example, at least 2.0 μm$^2$ per mm$^2$, at least 2.5 μm$^2$ per mm$^2$, at least 3.0 μm$^2$ per mm$^2$, at least 3.5 μm$^2$ per mm$^2$, at least 4 μm$^2$ per mm$^2$, at least 4.5 μm$^2$ per mm$^2$, at least 5 μm$^2$ per mm$^2$, at least 5.5 μm$^2$ per mm$^2$, at least 6.0 μm$^2$ per mm$^2$, at least 6.5 μm$^2$ per mm$^2$, at least 7.0 μm$^2$ per mm$^2$, at least 7.5 μm$^2$ per mm$^2$, or at least 8.0 μm$^2$ per mm$^2$, wherein a measured abundance of CD36-expressing vasculature below the selected threshold value is indicative of increased risk of progression to invasive breast cancer and a measured abundance of CD36-expressing vasculature above the selected threshold value is indicative of decreased or normal risk of progression to invasive breast cancer, for example, as found in the general population or in subjects without DCIS.

Methods of Treatment In another aspect, the scope of the invention encompasses methods of treatment. The general method of treatment of the invention encompasses the steps:

- by the abundance of CD36-expressing vasculature in a sample comprising precancerous tissue obtained from a subject, determining the likelihood of an invasive event for the subject; and
- administering an appropriate treatment based on the assessed risk of progression.

The appropriate treatment may be selected based on the standard of care for the cancer type at issue, the subject's additional risk factors (e.g. health history, genetics, etc.) and the subject's tolerance of risk. For example, in the case of invasive breast cancer, a more aggressive treatment such as radiation, hormonal therapy, chemotherapy, or mastectomy may be selected upon a determination of high risk of an invasive event, whereas, if a low risk of an invasive event is determined, aggressive treatments may be foregone in favor of watchful waiting.

In another aspect, the scope of the invention encompasses novel methods of treatment based on the identification of CD36 repression in vasculature as a causative agent of invasive cancer. The novel method of treatment comprises the delivery of CD36 enhancing agents to vasculature, for example, the targeted (e.g. selective or preferential) delivery of agents to such cells. While enhancement of CD36 has been previously suggested in the prevention and treatment of cancer, the discoveries disclosed herein provide the art with a novel cellular target for enhanced CD36 expression, in the stromal microvasculature. The CD36 enhancing agent may comprise an agent which enhances CD36 expression or activity in the vasculature or an agent which recapitulates the effects of CD36 expression in the vasculature. Alternatively, the agent may comprise a gene therapy construct for the transduction of vascular cells for increased expression of CD36 in target cells. Delivery to vasculature may be achieved by methods known in the art for the selective or preferential transformation of vascular cells, for example, by methods of delivering transgenes to be expressed in vascular compartments. The scope of the invention encompasses a composition for use in a method of preventing the occurrence of progressive cancer in a subject, the composition comprising an agent which selectively or preferentially enhances CD36 expression in the stromal microvasculature of the subject. Methods for targeted delivery to blood vessels may be adapted from methods known in the art, for example, those described in United States Patent Application Publication Number 20050053590, entitled "Endothelium-targeting nanoparticle for reversing endothelial dysfunction," by Meininger; PCT International Patent Application Publication Number 2002042426, entitled "Carrier system for specific artery wall gene delivery," by Yu et al.; and United States Patent Application Publication Number 20090209630, entitled "Gene delivery formulations and methods for treatment of ischemic conditions," by Coleman et al. Agents could be administered in a pharmaceutically effective amount to subjects in need of treatment, for example, subjects having precancerous lesions and, by the methods of the invention, found to be at elevated risk of progression to invasive cancer.

Kits for Assessing CD36-Expressing Vasculature Abundance. In another aspect, the scope of the invention encompasses novel kits for performing detection and/or quantification of CD36 expression in vasculature. Such kits will comprise a collection of items or compositions of matter that may be used in combination to label and/or quantify total vasculature and CD36-expressing vasculature. In one embodiment, the kit of the invention comprises immunohistochemical components, including anti-CD36 antibodies, antibodies to one or more markers of vascular/mesenchymal identity (e.g., vimentin), for example, fluorescent or enzymatically labeled antibodies, or secondary antibodies, for visualization/quantification. The kit may further comprise elements for the labeling and quantification of endothelial cells, e.g., CD31-expressing cells. In one embodiment, the kit comprises a triplex module for detection of CD36, CD31, and one or more mesenchymal identity markers (e.g., vimentin). In some embodiments, the kit comprises DAPI or a like stain to define nuclei or cellular morphology. In some embodiments, the kit comprises an epithelial cell marker for delineating the border of the stromal tissue to be analyzed, such as CD19, cadherin, or claudin.

In an alternative embodiment, the kit comprises elements for performing flow cytometry or like methods of cell counting. In another embodiment, the kit comprises a kit for quantitative PCR analysis, for example, primers for the selective amplification of CD36 transcripts, mesenchymal marker transcripts (e.g. vimentin), and CD31 transcripts.

Exemplary Embodiments

In a various implementations the invention encompasses method of determining the risk of progression to invasive cancer in a subject having a precancerous lesion, comprising the steps of obtaining a sample from the subject comprising stromal tissue adjacent to the precancerous lesion; analyzing the sample to determine the abundance of CD36-expressing vasculature in the stromal tissue adjacent to the precancerous lesion; and by the measured abundance of CD36-expressing vasculature, determining the risk of an invasive cancer progression in the subject, wherein a reduced abundance of CD36-expressing vasculature in the stromal tissue adjacent to the precancerous lesion in indicative of increased cancer progression risk, wherein the invasive cancer is selected from the group consisting of breast cancer, bladder cancer, brain cancer, cervical cancer, colorectal cancer, esophageal cancer, head and neck cancer, kidney cancer, lung cancer, leukemia, lymphoma, myeloma, ovarian cancer, pancreatic cancer, prostate cancer, sarcoma, and skin cancer; wherein in one embodiment, the invasive cancer is breast cancer and the precancerous lesion comprises DCIS; wherein in various implementations, the stromal tissue adjacent to the precancerous lesion comprises tissue within 0.5 to 2.0 mm of the lesion border, or in the case of healthy tissue, the epithelial cell border, wherein in one embodiment vimentin expression is utilized as a marker of mesenchymal vasculature; wherein in one implementation, the risk of invasive cancer progression is determined by comparing the measured abundance of CD36-expressing vasculature to a selected threshold value, wherein a measured abundance of CD36-expressing vasculature below the selected threshold value is indicative of elevated risk of progression to invasive cancer; wherein in some implementations, the threshold value is defined as a value selected from the group of: a value below the mean or median abundance of CD36-expressing vasculature in like healthy tissue in like subjects (in various embodiments subjects matched by medical history, demographics, and/or type of precancerous lesion; the value being a value at least one, two, or three standard deviations below the mean or median abundance of CD36-expressing vasculature in like healthy tissue in like subjects; a value threshold associated with increased risk of progression as established by predictive models for like tissues in like subjects; and a value at least 10%, 20%, 30%, 40%, 50%, 60%, 70%, 80%, or 90% lower than the mean or median abundance of CD36-expressing vasculature in like healthy tissue in like subjects;

in some implementations, the abundance of cd36-expressing vasculature is measured by immunohistochemical analysis in samples comprising tissue sections, wherein CD36-expressing vasculature abundance is measured as area; wherein in one implementation, the abundance of CD36-expressing vasculature is measured as a relative proportion of CD36-expressing vasculature in the stromal tissue adjacent to the precancerous lesion; wherein in one implementation, the relative abundance of CD36-expressing vasculature is determined by the ratio:

$$\frac{[CD36+/CD31-]+[CD36+/CD31+]}{[CD36+/CD31-]+[CD36+/CD31+]+[CD36-/CD31+]}$$

wherein $[CD36^+/CD31^-]$ denotes the abundance of CD36-positive and CD31-negative vasculature in the stromal tissue adjacent to the precancerous lesion, $[CD36^+/CD31^+]$ denotes the abundance of CD36-positive and CD31-positive vasculature in the stromal tissue adjacent to the precancerous lesion, and $[CD36^-/CD31^+]$ denotes the abundance of CD36-negative and CD31-positive vasculature in the stromal tissue adjacent to the precancerous lesion; wherein the selected threshold value is between 50% and 75%; in some implementations, the selected threshold value being between 60% and 70%; and in some implementations, the relative abundance of CD36-expressing vasculature is measured as the proportion of area of CD36-expressing vasculature in the total area of analyzed stromal tissue adjacent to the lesion; wherein the risk of invasive cancer progression is determined by comparing the measured abundance of CD36-expressing vasculature to a selected threshold value, wherein a measured abundance of CD36-expressing vasculature below the selected threshold value is indicative of elevated risk of progression to invasive cancer; and wherein the selected threshold value is between 2 and 30 $\mu m^2$ per $mm^2$; in some implementations, a value between 2 and 30 $\mu m^2$ per $mm^2$, in some implementations, a value between 2 and 10 $\mu m^2$ per $mm^2$ 13, in some implementations being a value between 4 and 6 $\mu m^2$ per $mm^2$.

In various embodiments, the scope of the invention encompasses methods of treating a subject having one or more precancerous lesions, comprising the steps of: by the foregoing described methods, determining the subject's risk of progression to invasive cancer; and administering an appropriate treatment based on the assessed risk of an invasive event, wherein in some embodiments, if the risk of progression to invasive cancer is elevated, one or more treatments selected from resection, radiation, chemotherapy, and hormonal treatment, is administered; and wherein, if the if the risk of progression to invasive cancer is low, no treatment intervention is administered; wherein in one embodiment, the invasive cancer is breast cancer and the precancerous lesion comprises DCIS and if the risk of progression to invasive cancer is elevated, one or more treatments selected from resection, mastectomy, radiation, chemotherapy, and hormonal treatment, is administered.

In some implementations, the scope of the invention encompasses a method preventing progression from precancerous lesion to invasive cancer in a subject by the administration of an agent which selectively or preferentially enhances CD36 expression in vasculature of the subject; in various implementations, the agent being selected from the group consisting of a CD36 agonist, CD36 mimic, or a gene therapy construct for the expression of CD36, wherein such agent is selectively or preferentially delivered to vasculature.

In some implementation, the scope of the invention encompasses a kit for the measurement of the relative abundance of CD36-expressing vasculature, comprising a detection agent selective for CD36-expressing cells; and one or more detection agents selective for vascular endothelial cells, wherein in one embodiment the one or more detection agent selective for vascular endothelial cells comprises a detection agent selective for vasculature, in one embodiment the detection agent being selective for vimentin-expressing cells; in one embodiment, the kit further comprising one or more detection agents selective for CD31-expressing cells; wherein in certain embodiments the detection agents comprise labeled antibodies or antigen binding fragments thereof, or antibodies or antigen binding fragments comprising an epitope for binding of labeled secondary antibodies; wherein in one embodiment, the kit comprises the kit comprises a triplex immunohistochemical module for detection of CD36, CD31, and vimentin; in one embodiment the kit comprises reagents for a flow cytometry or cell counting assay; in one embodiment the kit comprises reagents for a quantitative PCR assay comprising primers for the detection of CD36 and optionally, CD31, and vascular markers, in one embodiment vimentin.

EXAMPLES

Example 1. Predicting Risk of Subsequent Invasive Events in Women Diagnosed with DCIS by Assessing Vascular Phenotypes Ductal carcinoma in situ (DCIS) is a heterogeneous group of non-invasive breast lesions commonly detected by screening mammography. A small proportion of women diagnosed with DCIS subsequently develop potentially lethal invasive breast cancer (IBC). Ductal carcinoma in situ (DCIS) is the accumulation of neoplastic cells within the ducto-lobular system of the breast. Lack of invasion into the adjacent stroma is the key histological feature differentiating DCIS from invasive breast cancer (IBC). To date, there is currently insufficient data on the clonal relationship between primary DCIS and subsequent IBC to estimate the proportion of DCIS lesions actually capable of progressing to IBC, if left untreated.

DCIS currently accounts for 25-30% of all breast cancer diagnoses (60,000-70,000 cases per year in USA). DCIS is nearly universally treated by mastectomy or lumpectomy followed by adjuvant radiation and/or hormone therapy. However, despite the aggressive treatment of DCIS, the overall incidence of IBC or advanced IBC has not conspicuously declined. Prospective randomized trials of adjuvant radiation found that following lumpectomy alone, between 26% and 36% of women subsequently develop IBC with median follow-up ranging from 13 to 20 years. A course of radiotherapy following lumpectomy can decrease by approximately 50% the risk of developing subsequent ipsilateral IBC. However, this reduction in risk comes at the expense of significant overtreatment of women who would have never developed IBC. One study estimates that it is necessary to treat, with a five-week course of radiotherapy, 36 women diagnosed with DCIS to prevent one ipsilateral IBC during five years of follow-up. However, despite the overall favorable prognosis of women diagnosed with DCIS, a small percentage of these women, who will eventually develop metastatic IBC, would benefit from more aggressive therapy. Risk stratification models incorporating known biomarkers that distinguish potentially lethal DCIS lesions from abundant harmless ones are not informative for all DCIS lesions. The development and validation of additional biomarkers is therefore among the highest research priorities for improving the management of DCIS.

To address limitations of the prior art in risk stratification, the stroma was examined as a source of novel biomarkers. Stromal cell types adopt distinct, pro-tumorigenic states that support malignant progression. Moreover, stromal gene expression has been shown to predict clinical outcome in IBC. In the present Example, it is found that loss of vascular (stromal) CD36 expression predicts the likelihood of a subsequent IBC in women diagnosed with DCIS and treated by lumpectomy alone. High vascular CD36 identifies a group of women diagnosed with DCIS at low risk of developing potentially lethal IBC and therefore least likely to benefit from adjuvant therapy. Conversely, women with the lowest levels of vascular CD36 have an elevated risk of developing potentially lethal IBC and could potentially benefit from aggressive adjuvant therapy and/or increased surveillance.

Results. Characterization of CD36 repression in the stroma during development of IBC. The present Example illustrates the use of CD36 as a novel biomarker of transition from in situ to invasive carcinoma. CD36 expression was examined by immunohistochemistry (IHC) in DF breast, pure DCIS (i.e. without evidence of stromal invasion) and IBC. Adipocytes and the vasculature, particularly the intralobular capillary endothelium, stain positive for CD36 in DF tissues. Since adipocytes were largely absent from the desmoplastic stroma directly surrounding IBC, these were manually excluded from the quantitative analysis across all specimens. Selected for analysis was only the ECM-rich stromal areas directly adjacent to epithelium. As a percentage of the total area analyzed, DF breast tissue expressed significantly higher CD36 compared to IBC (8.3% vs 1.4%, respectively). CD36 expression in DCIS (4.9%) was variable and failed to reach a statistically significant difference when compared to DF breast. However, CD36 expression in DCIS specimens appear to span CD36 expression profiles of DF breast and those of IBC.

CD36 expression has been described in a variety of stromal cell types, including endothelial cells, macrophages, fibroblasts and adipocytes. To determine which stromal cell populations express CD36 in DF breast, and therefore account for its loss during development of IBC, multiplex IHC was utilized. This analysis was performed in three DF breast specimens with identical results. CD36 expression was absent from the breast epithelium as defined by pancytokeratin staining, but strongly expressed by mesenchymal elements within the stroma, as indicated by co-localization with vimentin, including adipocytes. CD36 expression was observed in rare $CD68^{+}$ macrophages and $CD31^{+}$ endothelial cells, but absent in podoplanin $(PDPN)^{+}$ lymphatic endothelial cells and Mannose Receptor C Type 2 $(MRC2)^{+}$ fibroblasts. Fibroblast-specific markers are particularly difficult to define, however MRC2 is a highly consistent marker of fibroblasts in the IHC-based assays described herein.

A shift in the proportion of CD36-expressing endothelial cells to CD31-expressing endothelial cells characterizes development of IBC. Even commonly utilized "pan-vascular" markers, including CD31, demonstrate significant heterogeneity within vascular networks. Vascular structures that express both CD36 and CD31 were identified, as well as, CD36 or CD31 alone. Both CD36 and CD31 can be expressed in subsets of immune cells, therefore a multiplex IHC scoring system was developed that evaluated CD31 and CD36 expression only in vimentin-expressing endothelial cells. Prior to quantitative analysis, adipocytes were manually masked out. The total vascular area that expressed CD36-alone, CD31-alone or co-expressed CD31 and CD36 in the stroma $(vimentin^{+})$ directly adjacent to epithelium was calculated in DF breast, DCIS, and IBC. The analysis performed on DF breast reveals significant variability in the relative proportion of CD36 and CD31 vascular phenotypes between donors. Breast density likely contributes to variation in CD36 expression, based previously published results, however mammographic density data was not available for donors included in the present study. Multiplex IHC analysis of IBC revealed that CD36-expressing vasculature is consistently low within the tumor area whereas CD31-expressing vasculature is dominant. This was observed in several IBC subtypes ($ER^{+}PR^{+}HER2^{-}$ [n=18], $ER^{-}PR^{-}HER2^{-}$ [n=7], $ER^{+}PR^{+/-}HER2^{+}$ [n=3], $ER^{-}PR^{-}HER2^{+}$ [n=4] and unknown status [n=8]). Direct comparison of total CD36 expression ($CD36^+$ and $CD36^+CD31^+$) within the vascular compartments of DF breast (median 53.5%, S.D. 17.8%) and IBC (median 11.7%, S.D. 11.9%) confirmed a highly significant decrease in CD36 staining within tumor areas.

Next, CD36 and CD31 vascular phenotypes were assessed in DCIS specimens collected following lumpectomy focusing on the vasculature directly adjacent to DCIS lesions. On the basis of CD36 and CD31 staining, the vasculature surrounding some DCIS lesions appears similar to DF breast-associated vasculature while the vasculature surrounding other DCIS lesions appears similar to IBC-associated vasculature. Long-term outcome was known for all 88 DCIS specimens including 57 controls without subsequent IBC and 31 cases who developed a subsequent IBC with a median follow-up of 15 years. On the basis of CD36 and CD31 staining, the vasculature surrounding DCIS lesions that do not progress to IBC (controls) appear, on average, similar to DF breast-associated vasculature, while the vasculature surrounding DCIS lesions that do progress to IBC appear, on average, more similar to IBC-associated vasculature. Direct comparison of total CD36 expression in DCIS cases and controls demonstrated that a significantly higher proportion of the total vasculature surrounding DCIS lesions expressed CD36 in controls (median 56.9%, S.D. 27.7%) compared to cases (median 19.4%, S.D. 27.4%).

Loss of vascular expression of CD36 predicts the risk of subsequent IBC in patients diagnosed with DCIS. Proportional representation as describe above provides one measure of CD36-expressing vasculature abundance. In additional analyses, total staining area of CD36 or CD31 normalized to the total assay area ($\mu m^2$ per $mm^2$) was used. Using this measure, CD36 area was observed to be significantly lower in IBC compared to DF breast and in DCIS lesions of cases compared to controls. Using a median (4.8 $\mu m^2$ per $mm^2$) cut-off, high levels of vascular CD36 were associated with an 80% greater event-free survival (Hazard Ratio (HR)=0.2, CI 0.086-0.47, p=0.0002) when considering all types of subsequent IBC events and a 82% greater event-free survival (HR=0.18, CI 0.037-0.88, p=0.034) for regional or distant metastatic disease. The selection of this median cut-off splits the cohort into two groups with a 5-fold difference in IBC incidence. The difference in outcome is most pronounced at the extremes of the distribution. Comparing the highest quartile in CD36 expression to the lowest quartile identifies a 7.3-fold difference in the risk of subsequent IBC (HR=0.14, CI 0.039-0.48, p=0.002). In addition, there were no cases associated with regionally or distantly metastatic IBC in the highest CD36 expression quartile compared to four cases in the lowest CD36 expression quartile.

In contrast, the CD31 area by itself was not significantly different between DF breast and IBC. DCIS cases exhibit a significantly higher level of CD31 compared to DCIS control, however CD31 area does not significantly stratify a woman's risk for developing subsequent IBC if considering all events or regionally/distantly metastatic events. Thus, CD31 area is not a significant predictor of subsequent IBC in Cox Proportional Hazards regression analysis.

Discussion. Overall, the results of this pilot study support the conclusion that a loss of vascular CD36 predicts an increased likelihood of subsequent IBC in women diagnosed with DCIS and treated by lumpectomy alone. Conventional risk stratification models classify DCIS based on clinical and histological features. While these factors remain important, the integration of novel biomarkers capable of further stratifying risk is essential to the development of sufficiently robust risk models that clinicians and women can feel comfortable consulting when facing treatment decisions. Recently developed clinical risk models (i.e. DCISionRT and Oncotype DX DCIS) have begun the process of combining novel biomarkers with traditional clinicopathological parameters to better estimate risk.

As demonstrated in this Example, evaluation of CD36 expression in the stromal vasculature surrounding DCIS lesions enables stratification of risk for developing subsequent IBC. With a median follow-up of 15 years, 64% of women in the lowest vascular CD36 expression quartile developed subsequent IBC (32% regional/metastatic) compared to 14% of women in the highest vascular CD36 expression quartile (0% regionally metastatic). The capacity of vascular CD36 to define a group of women at low risk of developing potentially lethal IBC may support efforts to reduce the utilization of adjuvant therapy in women diagnosed with DCIS. Conversely, the identification of a group of women at high risk of subsequent IBC may enable appropriate administration of more aggressive treatments for women identified as higher risk.

Previous studies of the association between vasculature and tumor progression for risk stratification have concentrated on microvessel density, a semi-quantitative measure of vascular structures within the tumor stroma based on the expression of widely expressed endothelial cell markers (e.g. CD31, vWF and CD34). In meta-analysis, microvessel density was found to be a weak prognostic factor in women with IBC. In DCIS, high microvessel density is associated with stromal desmoplasia, HER2 expression and high proliferation index, but has not been evaluated respective to outcome. Herein, no correlation between CD31 and risk of subsequent IBC following a primary DCIS diagnosis and treatment with lumpectomy was found. This Example demonstrates a novel approach to considering the relationship between the vasculature and risk stratification, based on vascular phenotype (quality rather than quantity).

In DF breast tissue, CD36 is predominantly expressed by endothelial cells in the capillary beds adjacent to epithelial structures. In contrast, larger capacity vessels (e.g. venules and arterioles) tend to express CD31 instead. Phenotypic heterogeneity is observed throughout the vascular tree. In endothelial cells, CD36 serves as a receptor for thrombspondin-1 (TSP-1) contributing to repression of angiogenesis. Tumorigenesis is associated with irregular vascular networks, vast changes in hemodynamics and the efficiency of tissue perfusion.

The majority of biomarkers previously proposed for risk stratification of DCIS have concentrated on the epithelial component of the tumor. Markers that covariate with aggressive epithelial phenotypes are likely to predict which lesions contain or have the propensity to develop a subpopulation of cells capable of breaching the basement membrane, invading and surviving within the adjacent breast stroma. However, intrinsic cellular programs are not exclusively responsible for determining epithelial phenotypes. Reciprocal interactions between stromal and epithelial cells are important determinants of cellular phenotype. In addition to establishing organ-appropriate barrier function, endothelial cells also provide organ-specific cues, termed angiocrine factors, which guide aspects of tissue morphogenesis, regeneration/repair, homeostasis and tumorigenesis. Stromal biomarkers increase the prognostic acumen of risk stratification models for both pre-malignant and malignant conditions.

Methods. Staining of Archival Specimens: Specimens of DF breast tissue were collected from reduction mammoplasty surgery. IBC specimens and DCIS specimens were obtained. Sections (5 μm thick) were cut from formalin-fixed paraffin embedded tissue blocks. Slides were baked at 60° C., deparaffinized in xylene, rehydrated in graded ethanols and distilled $H_2O$. Endogenous peroxidases were quenched with 3% $H_2O_2$ diluted in PBS. Heat induced antigen retrieval was performed in citrate buffer pH 6.0 at 95° C. for 15 minutes. Non-specific antibody binding was reduced using the background reducer. Slides were incubated overnight at 4° C. with CD36 antibody (Cell Signaling Technology [CST], Clone: D8L9T) diluted 1:200 in antibody diluent, washed in TB ST (0.05 M Tris-HCl pH 7.5, 0.15M NaCl, 0.05% Tween-20) and then incubated with horseradish peroxidase polymer for 30 minutes. After washing in TBST, slides were incubated for three minutes with sensitive HRP substrate, washed in $dH_2O$, counterstained with Mayer's hematoxylin and permanently mounted. For multiplex IHC, a similar protocol was followed iteratively for each antibody: CD36 (Clone: D8L9T, 1:2000), CD31 (Clone: JC70A, 1:1000, Agilent Dako), Vimentin (Clone: 3B4, 1:6000, Agilent Dako); Pan-cytokeratin (Agilent Dako, Clone: AE1/AE3, 1:6000); CD68 (CST, Clone: PG-M1, 1:2000), PDPN (AbCAM, Clone: D4-20, 1:4000) or MRC2 (AbCAM, Polyclonal, Cat. #ab70132, 1:2000). However, slides were washed with TNT buffer (0.1 M TRIS-HCL pH 7.5, 0.15M NaCl and 0.05% Tween-20), primary incubation was one hour at room temperature and the slides were developed with tyramide signal amplification solution: FITC (2 minutes), Cy3 (3 minutes) or Cy5 (7 minutes). Removal of the antibody complex between markers was achieved by heating in 95° C. citrate buffer pH 6.0 for 5 minutes. Nuclei were counterstained with 1 μM DAPI in PBS for 5 minutes, washed in distilled water and mounted with mounting media.

Imaging: Standard IHC-stained slides were imaged (20×) using an whole slide scanner. Multiplex IHC-stained slides were imaged using a microscope equipped to image DAPI, FITC, Cy3, and Cy5. Fluorescence spectra were recorded from 420 nM to 720 nM at 20 nM increments with a multispectral imaging system. All imaging was performed using a 20× air objective (Leica).

Data Analysis: Analysis of standard IHC-stained sections was performed using Qupath software (v0.2.0-m3). Stain vectors and threshold were estimated for DAB using a representative image of DF breast. After masking the regions of interest (ROIs) for analysis, the positive pixel count command was utilized to determine the DAB-positive area ($\mu m^2$). The DAB-positive area was divided by the total area of the ROI to estimate the percentage of total area expressing CD36. For analysis of multiplex IHC-stained slides, a spectral library was generated by collecting fluorescence spectra from slides singly stained with each fluorophore then subtracting the background fluorescence spectra (generated from an unstained slide). Spectral processing using this library was performed with software for the separation of DAPI, FITC, Cy3 and Cy5 signals. From each specimen at least five fields were analyzed to determine co-localization. Area was converted to $\mu m^2$ and divided by the total $mm^2$ area analyzed to estimate $CD36^+$, $CD31^+$ and $CD36^+/CD31^+$ areas in $\mu m^2$ per $mm^2$.

Statistical analysis: Pairwise comparisons were performed using the Wilcoxon/Kruskal-Wallis rank of sums test. Levels of significance used were *<0.01, <0.001 and *<0.0001. Staining, imaging and scoring of the DCIS cohort was performed blinded to outcome. An event was defined as a subsequent ipsilateral IBC diagnosed at least six months after the initial diagnosis of DCIS. Kaplan-Meier method was utilized to compare the event-free survival of patients between groups. Statistical analysis was performed by Log-rank test. Cox proportional hazards models were applied to determine hazard ratios (HRs) for both CD36 and CD31 using the Survival package (version 2.44-1.1) in R (version 3.6.1).

Example 2. CD36+ Vasculature Abundance in Colon

The abundance of CD36-expressing vasculature was measured in stromal tissue adjacent to healthy colon epithelia (5 subject), in stromal tissue adjacent to IBD lesions (9 subjects), and in stromal tissue adjacent to invasive colon cancer tumors (8 subjects). The abundance of CD36-expressing vasculature (CD36+/CD31−+CD36+/CD31+) was measured as the percentage of all vasculature [CD36+/CD31−+CD36+/CD31++CD36−/CD31+]. The percentage of CD36-expressing vasculature was high in healthy tissues (~70-95%) and substantially lower in stromal tissue adjacent to invasive colon tumors (~30% or lower in seven of eight subjects). The abundance of CD36-expressing vasculature varied in stromal tissues surrounding IBD lesions. These results suggest repression of CD36-expressing vasculature in the progression from healthy to cancerous tissue.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of treating a subject having a precancerous lesion and identified as being at risk of progression to invasive cancer, comprising the steps of obtaining a sample from the subject comprising stromal tissue adjacent to the precancerous lesion;

measuring the abundance of CD36-expressing vasculature in the stromal tissue adjacent to the precancerous lesion, determining the risk of an invasive cancer progression in the subject, wherein when the measured abundance of CD36-expressing vasculature in the stromal tissue adjacent to the precancerous lesion is below a threshold value, the measured abundance is then indicative of increased cancer progression risk in the subject, wherein the threshold value is a median or mean abundance value of CD36-expressing vasculature observed in healthy stromal tissue; and administering a treatment to the subject identified as having an increased cancer progression risk, wherein the treatment is selected from the group consisting of radiation, hormonal therapy, chemotherapy, and mastectomy.

2. The method of claim 1, wherein the invasive cancer is selected from the group consisting of breast cancer, bladder cancer, brain cancer, cervical cancer, colorectal cancer, esophageal cancer, head and neck cancer, kidney cancer, lung cancer, leukemia, lymphoma, myeloma, ovarian cancer, pancreatic cancer, prostate cancer, sarcoma, and skin cancer.

3. The method of claim 2, wherein the invasive cancer is breast cancer and the precancerous lesion comprises DCIS.

4. The method of claim 1, wherein the stromal tissue adjacent to the precancerous lesion comprises tissue within 0.5 to 2.0 mm of the lesion border.

5. The method of claim 1, wherein the abundance of CD36-expressing vasculature is measured by immunohistochemical analysis in samples comprising tissue sections, wherein CD36-expressing vasculature abundance is measured as area.

6. The method of claim 1, wherein the measured abundance of CD36-expressing vasculature in the stromal tissue adjacent to the precancerous lesion is at least 50% lower than the median or mean abundance value of CD36-expressing vasculature observed in healthy stromal tissue.

7. The method of claim 6, wherein the measured abundance of CD36-expressing vasculature in the stromal tissue adjacent to the precancerous lesion is at least 60% lower than the median or mean abundance value of CD36-expressing vasculature observed in healthy stromal tissue.

* * * * *